(12) United States Patent
Cormier

(10) Patent No.: US 10,379,088 B2
(45) Date of Patent: Aug. 13, 2019

(54) SYSTEM AND METHOD FOR PERFORMING A CHROMATOGRAPHY INJECTION SEQUENCE USING A SINGLE INJECTION VALVE

(71) Applicant: Waters Technologies Corporation, Milford, MA (US)

(72) Inventor: Sylvain Cormier, Mendon, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 33 days.

(21) Appl. No.: 15/527,182

(22) PCT Filed: Nov. 2, 2015

(86) PCT No.: PCT/US2015/058571
§ 371 (c)(1),
(2) Date: May 16, 2017

(87) PCT Pub. No.: WO2016/089515
PCT Pub. Date: Jun. 9, 2016

(65) Prior Publication Data
US 2017/0336369 A1      Nov. 23, 2017

Related U.S. Application Data

(60) Provisional application No. 62/085,960, filed on Dec. 1, 2014.

(51) Int. Cl.
*G01N 30/20* (2006.01)
(52) U.S. Cl.
CPC ....... *G01N 30/20* (2013.01); *G01N 2030/202* (2013.01); *G01N 2030/207* (2013.01)

(58) Field of Classification Search
CPC .. G01N 30/16; G01N 30/20; G01N 2030/027; G01N 2030/201; G01N 2030/202; G01N 2030/207
(Continued)

(56) References Cited

U.S. PATENT DOCUMENTS

2012/0132013 A1    5/2012   Glatz et al.
2013/0056084 A1    3/2013   Dourdeville et al.
(Continued)

OTHER PUBLICATIONS

International Search Report and Written Opinion in counterpart International Patent Application No. PCT/US15/58571, dated Jan. 22, 2016; 9 pages.
(Continued)

*Primary Examiner* — Benjamin R Schmitt
(74) *Attorney, Agent, or Firm* — Schmeiser, Olsen & Watts LLP

(57) ABSTRACT

A rotary valve used in chromatography includes a stator with a plurality of stator ports arranged on the stator. The stator further includes a stator groove connected at one end to a first stator port and terminating between the first stator port and a second stator port adjacent to the first stator port. A rotor, rotatably fitted to the stator, has a plurality of arcuate channels arranged in an asymmetrical pattern on the rotor. Each rotor channel connects to one or more of the stator ports. Different connections of the rotor channels to the stator ports produce at least three different positions for the injection valve. The three different positions provide a complete chromatography sample injection sequence using only a single valve.

19 Claims, 11 Drawing Sheets

(58) Field of Classification Search
USPC ........... 73/61.41, 61.43, 61.52, 61.55, 61.56, 73/863.71, 863.72
See application file for complete search history.

(56) References Cited

U.S. PATENT DOCUMENTS

| | | |
|---|---|---|
| 2013/0067997 A1 | 3/2013 | Ebsen et al. |
| 2013/0068977 A1 | 3/2013 | Picha et al. |

OTHER PUBLICATIONS

International Preliminary Report in International Patent Application No. PCT/US15/58571, dated Jun. 15, 2017; 8 pages.

SYSTEM AND METHOD FOR PERFORMING A CHROMATOGRAPHY INJECTION SEQUENCE USING A SINGLE INJECTION VALVE

RELATED APPLICATIONS

This application claims the benefit of the earlier filing date of U.S. Provisional Patent Application Ser. No. 62/085,960, filed Dec. 1, 2014 and titled "System and Method for Performing a Chromatography Injection Sequence Using a Single Injection Valve," the entirety of which is incorporated herein by reference.

FIELD OF THE INVENTION

The invention relates generally to chromatography systems. More specifically, the invention relates to chromatography sample managers with a single injection valve that can be used to perform an entire injection sequence.

BACKGROUND

Chromatography is a set of techniques for separating a mixture into its constituents. Generally, in a liquid chromatography analysis, a pump system takes in and delivers a mixture of liquid solvents (and/or other fluids) to a sample manager, where a sample is injected into the solvent stream. The sample is the material under analysis. Examples of samples include, but are not limited to, complex mixtures of proteins, protein precursors, protein fragments, reaction products, and other compounds. The mobile phase comprised of a sample dissolved in the mixture of solvents (and/or other fluids), moves to a point of use, such as a separation column, referred to as the stationary phase. By passing the mobile phase through the column, the various components in the sample separate from each other at different rates and thus elute from the column at different times. A detector may receive the separated components from the column and produce an output from which the identity and quantity of the analytes may be determined.

SUMMARY

All examples and features mentioned below can be combined in any technically possible way.

In one aspect, a sample manager comprises a sample loop and a single injection valve configured to (i) to depressurize the sample loop, (ii) draw a sample into the sample loop, and (iii) inject the sample in the sample loop into a pressurized fluidic stream. The injection valve has a stator and a rotor rotatably fitted to the stator. The stator has a plurality of stator ports arranged on the stator. In some embodiments, the stator ports can be circularly arranged on the stator. The stator further includes a stator groove connected at one end to a first one of the stator ports and terminating at an opposite end between the first stator port and a second one of the stator ports adjacent to the first stator port. The first stator port is fluidically coupled to a source of the pressurized fluidic stream. The second stator port is fluidically coupled to a destination of the pressurized fluidic stream. The rotor has a plurality of rotor grooves arranged in an asymmetrical pattern on the rotor. In some embodiments, the rotor grooves can be arcuate grooves. In various embodiments, the rotor grooves can be circularly arranged on the rotor, for example, in an asymmetrical pattern. For example, arcuate rotor grooves can be circularly arranged in an asymmetrical pattern on the rotor. Each of the rotor grooves connects to one or more of the stator ports. The injection valve has at least three different positions including a first position in which a first one of the rotor grooves connects the stator groove to the second stator port to enable the pressurized fluidic stream arriving at the first stator port to flow directly to the second stator port towards the destination while the sample loop depressurizes.

Embodiments of the sample manager may include one of the following features, or any combination thereof.

The sample manager may further comprise a flow-through needle connected to a third one of the stator ports and a pressure source connected to a fourth one of the stator ports. The at least three different positions of the injection valve includes a second position in which the first rotor groove connects the first stator port to the second stator port to enable the pressurized fluidic stream arriving at the first stator port to flow directly to the second stator port and a second one of the rotor grooves connects the third stator port to the fourth stator port to enable the pressure source to draw the sample from a sample source into the flow-through needle.

The sample manager may further comprise a seat into which the flow-through needle is driven and sealed. An outlet of this seat is connected to a fifth one of the stator ports. The at least three different positions of the injection valve includes a third position in which the second rotor groove connects the first stator port to the third stator port to enable the pressurized fluidic stream arriving at the first stator port to flow into the flow-through needle containing the sample and the first rotor groove connects the fifth stator port to the second stator port to enable the pressurized fluidic stream containing the sample to exit the sample loop and flow towards the destination. While the injection valve is in the second position and the flow-through needle is driven into and sealed by the seat, the pressure source may pressurize the sample loop containing the sample before the injection valve moves to the third position to inject the sample to the pressurized fluidic stream.

In another example, the sample manager may further comprise a flow-through needle connected to a third one of the stator ports adjacent the first stator port, a waste receptacle connected to a fourth one of the stator ports, a pressure source connected to a fifth one of the stator ports disposed between the third and fourth stator ports, and a seat into which the flow-through needle is driven and sealed. An outlet of this seat is connected to a sixth one of the stator ports. The at least three different positions of the injection valve includes a second position in which the sixth stator port is blocked, thereby blocking a flow through the sample loop; a second one of the rotor grooves connects the first, third, fourth, and fifth stator ports to enable the pressurized fluidic stream arriving at the first stator port to flow towards the waste receptacle through the fourth stator port so the pressure source can be primed.

In addition, the asymmetrical pattern of the rotor grooves on the rotor is produced by at least one of the rotor grooves having a different length than at least one of the other rotor grooves, by at least one gap between neighboring rotor grooves being greater than at least one other gap between neighboring rotor grooves, or by a combination thereof. One of the rotor grooves may have a length sufficient to connect together four adjacent stator ports. Further, the stator may have eight stator ports.

In another aspect, a method is provided of completely performing a chromatography injection sequence using only a single rotary valve having a stator and a rotor rotatably fitted to the stator. The stator has a plurality of stator ports arranged on the stator. In some embodiments, the stator ports can be circularly arranged on the stator. The stator further includes a stator groove connected at one end to a first one of the stator ports, an opposite end of the stator groove terminating between the first stator port and a second one of the stator ports that is adjacent to the first stator port, a third one of the stator ports being connected to an inlet of a sample loop, and a fourth one of the stator ports being connected to an outlet of the sample loop. The rotor has a plurality of rotor grooves arranged in an asymmetrical pattern on the rotor. In some embodiments, the rotor grooves can be arcuate grooves. In various embodiments, the rotor grooves can be circularly arranged on the rotor, for example, in an asymmetrical pattern. For example, arcuate rotor grooves can be circularly arranged in an asymmetrical pattern on the rotor. Each of the rotor grooves connects to one or more of the stator ports.

The method comprises delivering a pressurized fluidic stream to the first stator port, fluidically coupling the second stator port to a destination of the pressurized fluidic stream, and placing the rotary valve into a first position in which a first one of the rotor grooves connects the stator groove to the second stator port to cause the pressurized fluidic stream arriving at the first stator port to flow through the stator groove directly to the second stator port and towards the destination, while the first position of the rotary valve blocks the inlet and outlet of the sample loop, enabling the sample loop to depressurize. The method further includes changing the rotary valve from the first position to a second position in which the first rotor groove connects the first stator port to the second stator port to cause the pressurized fluidic stream arriving at the first stator port to flow directly to the second stator port, while enabling a sample to be drawn into the sample loop; and changing the rotary valve from the second position to a third position to redirect the pressurized fluidic stream arriving at the first stator port through the sample loop containing the sample before the pressurized fluidic stream flows to the second stator port towards the destination.

Embodiments of the method may include one of the following features, or any combination thereof.

Changing the rotary valve from the first position to the second position may include turning the rotary valve one-half step and changing the rotary valve from the second position to the third position may include turning the rotary valve one full step in a direction opposite a direction used to change the rotary valve from the first position to the second position.

The method may further comprise pressurizing the sample loop containing the sample while the rotary valve is in the second position before changing the rotary valve to the third position to inject the sample into the pressurized fluidic stream. Further, the method may further comprise connecting a flow-through needle to a third one of the stator ports and connecting a pressure source to a fourth one of the stator ports. While the rotary valve is in the second position, a second one of the rotor grooves connects the third stator port to the fourth stator port, a tip of the flow-through needle is inserted into a source of sample, and the pressure source draws the sample from the source through the tip into the flow-through needle. The method may further comprise driving the flow-through needle into a seat to produce a seal. The seat has an outlet connected to a fifth one of the stator ports. And while the rotary valve is in the third position, the second rotor groove connects the first stator port to the third stator port to enable the pressurized fluidic stream arriving at the first stator port to flow into the flow-through needle containing the sample, and first rotor groove connects the fifth stator port to the second stator port to enable the pressurized fluidic stream containing the sample to exit the sample loop and flow towards the destination.

The method may further comprise connecting a third one of the stator ports, adjacent the first stator port, to a flow-through needle, connecting a fourth one of the stator ports to a waste receptacle, connecting a fifth one of the stator ports, disposed between the third and fourth stator ports, to a pressure source, connecting a sixth one of the stator ports to an outlet of a seat, driving the flow-through needle into the seat to produce a seal, and turning the injection valve into a second position in which a sixth stator port is blocked, thereby blocking a flow through the sample loop. A second one of the rotor grooves connects the first, third, fourth, and fifth stator ports to enable the pressurized fluidic stream arriving at the first stator port to flow towards the waste receptacle through the fourth stator port. In addition, the method may further comprise priming the pressure source while the injection valve is in this second position.

In another example, the method may further comprise connecting a third one of the stator ports, adjacent the first stator port, to a flow-through needle, connecting a fourth one of the stator ports to a pressure source, connecting a fifth one of the stator ports to an outlet of a seat, driving the flow-through needle into an inlet of the seat to produce a seal, turning the injection valve from the first position into a second position in which the first rotor groove connects the first stator port to the second stator port to enable the pressurized fluidic stream arriving at the first stator port to flow directly to the second stator port, in which a second one of the rotor grooves connects the third stator port to the fourth stator port connected to the pressure source, and in which the fifth stator port connected to the outlet of the seat is blocked, and then performing a leak test by pressurizing the sample loop using the pressure source.

In still another aspect, a rotary valve used in chromatography comprises a stator having a plurality of stator ports arranged on the stator. In some embodiments, the stator ports can be circularly arranged on the stator. The stator further includes a stator groove. One end of the stator groove connects to a first one of the stator ports and an opposite end of the stator groove terminates between the first stator port and a second one of the stator ports adjacent to the first stator port. The rotary valve further comprises a rotor rotatably fitted to the stator. The rotor has a plurality of channels arranged in an asymmetrical pattern on the rotor. In some embodiments, the rotor grooves can be arcuate grooves. In various embodiments, the rotor grooves can be circularly arranged on the rotor, for example, in an asymmetrical pattern. For example, arcuate rotor grooves can be circularly arranged in an asymmetrical pattern on the rotor. Each of the rotor channels connects to one or more of the stator ports. Different connections of the rotor channels to the stator ports produce at least three different positions for the rotary valve. The three different positions of the rotary valve provide a complete chromatography sample injection sequence using only a single valve.

Embodiments of the rotary valve may include one of the following features, or any combination thereof.

The asymmetrical pattern of the rotor grooves on the rotor may be produced by at least one of the rotor grooves having a different length than at least one of the other rotor grooves, by at least one gap between neighboring rotor grooves being greater than at least one other gap between neighboring rotor grooves, or by a combination thereof. One of the rotor grooves may have a length sufficient to connect together four adjacent stator ports. The stator may have eight stator ports.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION

Chromatography sample managers described herein use only one valve to perform an entire sample injection sequence, whereby a sample is introduced to a pressurized solvent stream. This sole valve (hereafter "injection valve") is a rotary valve with asymmetrical channels (or grooves) in the rotor and a channel (or groove) in the stator. The channel in the stator enables depressurization of the sample loop before connecting the sample pump or syringe (hereafter "pressure source") to the sample loop, while maintaining a constant flow between the solvent delivery system and the column manager. The use of one injection valve simplifies troubleshooting should the sample manager require repair.

Figure 1:
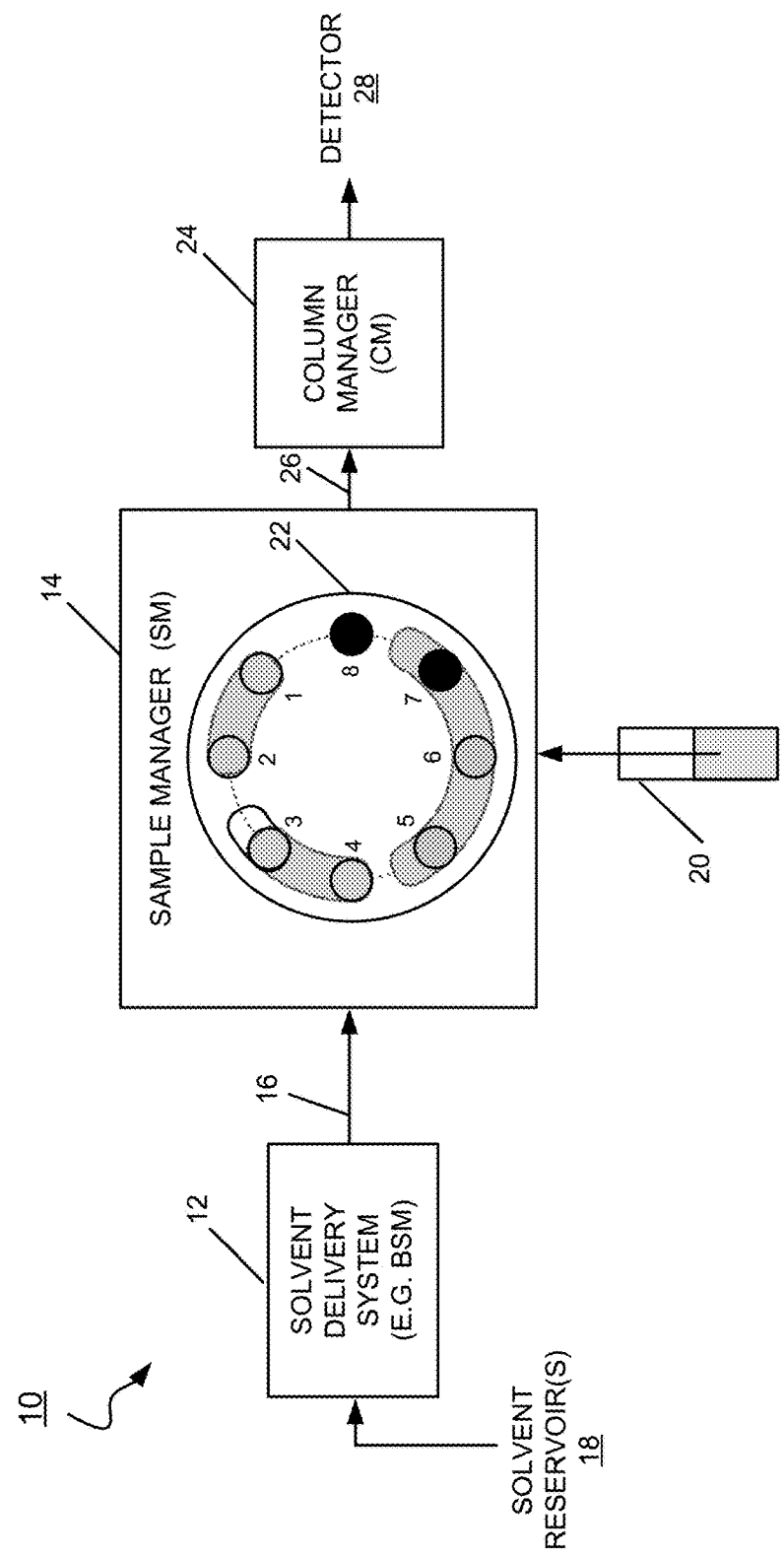
FIG. 1 is a diagram of an embodiment of a chromatography system with a sample manager that uses a single injection valve to perform an entire sample injection sequence.

FIG. 1 shows an embodiment of a chromatography system 10 for separating a mixture into its constituents. The chromatography system 10 includes a solvent delivery system 12 in fluidic communication with a sample manager (SM) 14 through tubing 16. Generally, the solvent delivery system 12 includes pumps (not shown) in fluidic communication with solvent reservoirs 18 from which the pumps draw solvents. In one embodiment, the solvent delivery system 12 is a binary solvent manager (BSM), which uses two individual serial flow pumps to draw solvents from their reservoirs 18 and deliver a solvent composition to the SM 14. An example implementation of a BSM is the ACQUITY UPLC Binary Solvent Manager, manufactured by Waters Corp. of Milford, Mass. The pumps of the BSM are capable of generating pressure as high as 18 K psi (pounds per square inch). Hereafter, for purposes of illustration by example, the solvent delivery system 12 may be referred to as a BSM 12.

The SM 14 is in fluidic communication with a sample source 20 from which the SM 14 acquires a sample. The sample source 20 can be, for example, a vial containing the sample, or a process line, from which the sample manager 14 acquires and introduces a sample to the solvent composition arriving from the solvent delivery system 12. The SM 14 includes a sample loop (not shown) and a single rotary injection valve 22 configured to suffice as the only valve used in the full execution of a sample injection sequence. In addition to simplifying the amount of hardware involved a sample injection sequence, use of a single injection valve can simplify troubleshooting should a repair of the SM 14 be needed. An example implementation of a sample manager that can be modified to use just one rotary injection valve to perform an entire sample injection sequence is the ACQUITY FTN Sample Manager, manufactured by Waters Corp. of Milford, Mass.

The SM 14 is also in fluidic communication with a column manager (CM) 24 by tubing 26 by which the solvent composition, with the injected sample, passes to the CM 24. The CM 24 generally provides a controlled temperature environment for one or more chromatography separation columns used in separating sample-solvent compositions. Each separation column is adapted to separate the various components (or analytes) of the sample from each other as the mobile passes through, and to elute the analytes (still carried by the mobile phase) from the column at different times. From the column manager 24, the constituents of the separated sample pass to a detector 28 or other equipment, for example, a mass spectrometer or a Flame Ionization Detector (FID), for analyzing the separation.

The chromatography system 10 further includes a data system (not shown) that is in signal communication with the solvent delivery system 12 and the SM 14. The data system has a processor and a switch (e.g., an Ethernet switch) for handling signal communication between the solvent delivery system 12 and SM 14. In addition, the data system is programmed to implement the various phases of operation performed by the SM (e.g., turning pumps on and off, rotating the injection valve 22) in order to inject the sample to a solvent composition stream, as described herein. In addition, a host computing system (not shown) is in communication with the data system, by which personnel can download various parameters and profiles to affect the data system's performance.

The solvent delivery system 12, SM 14, CM 24, and detector 28 may be separate instruments or integrated into a single unit.

Figure 2:
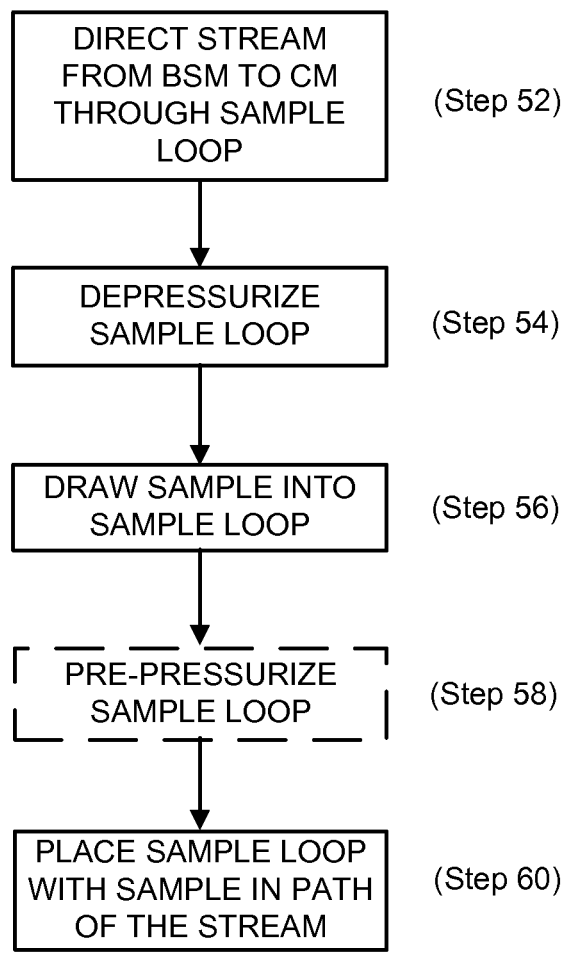
FIG. 2 is a flow diagram of an embodiment of a sample injection sequence performed by the sample manager using the single injection valve.

FIG. 2 shows an embodiment a sample injection sequence 50 by which the SM 14 introduces a sample into a solvent composition stream arriving from the solvent delivery system 12. At step 52, the injection valve 22 is in position to direct the pressurized solvent composition stream from the solvent delivery system 12 towards the CM 24 through a sample loop. To get a sample into the sample loop, the injection valve 22 is turned into a position that enables the sample loop to depressurize (step 54), while maintaining the flow of the pressurized solvent composition stream from the solvent delivery system 12 to the CM 24. After the sample loop depressurizes, the injection valve 22 is moved into a position that enables the sample to be drawn (step 56) from the sample source 20 into the sample loop, without disrupting the pressurized stream flowing from the solvent delivery system 12 to the CM 24. Optionally, the sample loop can then be pre-pressurized (step 58) before introducing the sample to the pressurized stream. Pre-pressurization of the sample loop limits the drop in pressure in the chromatography system 10 that would ordinarily result if a sample at low or atmospheric pressure were introduced to a pressurized stream. At step 60, the injection valve 22 moves into position in which the sample loop, containing the sample, is placed into the path of the pressurized solvent composition stream flowing from the solvent delivery system 12 to the CM 24.

Figure 3:
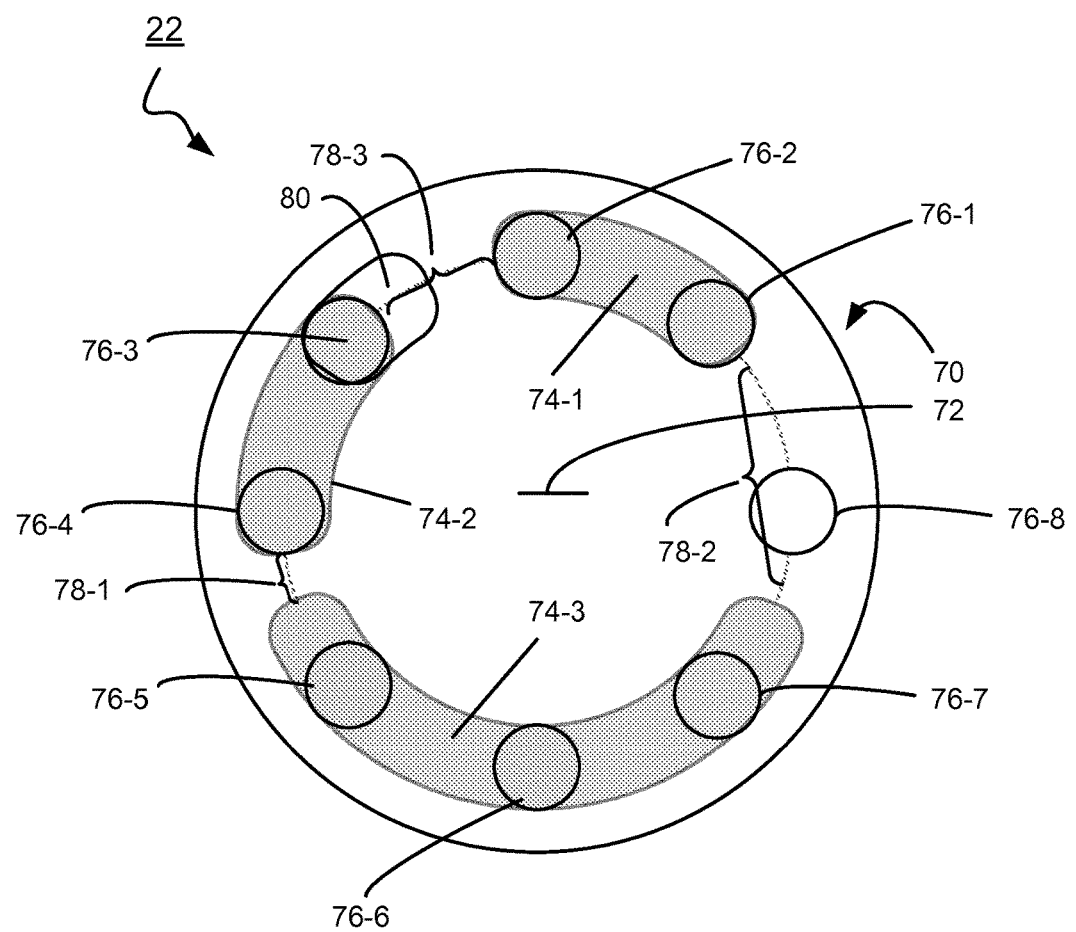
FIG. 3 is a diagram of an embodiment of an injection valve used to perform the sample injection sequence of FIG. 2.

FIG. 3 shows an embodiment of the injection valve 22 having a rotor 70 fitted to and, in FIG. 3, situated behind a stator 72; the rotor 70 rotates, while the stator 72 is the stationary part of the injection valve 22. The rotor 70 has a plurality of arcuate flow-through channels or grooves 74-1, 74-2, and 74-3 (generally, rotor groove 74), circularly arranged in the rotor 70. The channels can be 0.008" in width, 0.008" in depth, with 0.004" radius at the bottom of the groove. The circular arrangement of the rotor grooves 74 produce an asymmetrical pattern on a radius, 0.050", of the rotor 70. In general, the asymmetrical pattern of the arcuate rotor grooves 74 may be produced by at least one of the rotor grooves 74 having a different length than at least one of the other rotor grooves, by having gaps of different lengths between adjacent rotor grooves 74, or by a combination thereof (as is the instance in FIG. 3).

The stator 72 has a plurality of stator ports 76-1, 76-2 . . . 76-8 (generally, port 76) symmetrically disposed along a radius of the stator 72. In the shown embodiment, the stator 72 has eight stator ports 76. Other embodiments can have nine or more stator ports. The stator 72 also has a groove 80 with a length that spans half the distance between, and inclusive of, two adjacent stator ports 76. In this embodiment, the stator groove 80 connects to the stator port 76-3.

In this embodiment, the rotor groove 74-3 is longer than the other two rotor grooves 74-1, 74-2, which are equal in length; the rotor grooves 74-1 and 74-2 each spans the distance between (and including) two stator ports; the rotor groove 74-3 spans four stator ports. The length of each rotor groove 74-1, 74-2 is sufficient to connect together two adjacent stator ports 76; that of the rotor groove 74-3, to connect together four neighboring stator ports 76.

In addition, the gap 78-1 between rotor grooves 74-2 and 74-3 is the shortest of the three gaps 78-1, 78-2, 78-3. The gap 78-1 is about one-half the distance between two stator ports. The gap 78-2 between rotor grooves 74-1 and 74-3 is about one and one-half times the distance between two stator ports. The gap 78-3 between rotor grooves 74-1 and 74-2 is about the distance between two stator ports. The stator groove 80, which opens into the stator ports 76-3, extends across the gap 78-3 towards the stator port 76-2, extending midway between the stator ports 76-2, 76-3.

The rotor 70 can turn, relative to the stator 72, in discrete full steps or half steps. Each full step corresponds to a clockwise or counterclockwise turn equivalent to the length of an arc between two adjacent stator ports 76. When a rotor 70 rotates, its rotor grooves 74 move clockwise or counterclockwise, depending upon the direction of rotation. This movement can operate to switch the rotor grooves 74 to different pairs or groups of neighboring stator ports 76, establishing fluidic pathways between or among those stator ports 76, while removing pathways from the previously connected stator ports 76. The stator groove 80 enables depressurization of the sample loop, while maintaining a constant stream between the BSM 12 and the CM 24, as described in more detail in connection with FIG. 5.

FIG. 4, FIG. 5, FIG. 6, FIG. 7, and FIG. 8 correspond to the steps of 52, 54, 56, 58, and 60, respectively, of the injection sequence 50 described in connection with FIG. 2. Each of these figures shows an embodiment of the SM 14 having a flow-through-needle (FTN) mechanism used to inject a sample into a solvent composition stream. The SM 14 includes the injection valve 22, a needle 100, a needle drive 102, a seat 104, a pressure source 106, a transducer 108, a wash valve 110 connected to a wash pump 112, and a sample source 20 (here, e.g., a vial).

In each of these figures, the eight ports 76 of the injection valve 22 are connected to the various components of the SM 14 as follows: port 76-1 is connected by tubing 120 to an exit port of the seat 104; port 76-2 is connected by tubing 26 to the column manager 24; port 76-3 is connected by tubing 16 to the solvent delivery system 12; port 76-4 is connected by tubing 126 to the entry end of the needle 100; port 76-5 is connected by tubing 128 to the transducer 108; port 76-6 is connected by tubing 130 to waste 132; and ports 76-7 and 76-8 are unused and plugged.

In general, the needle 100 is part of the sample loop of the SM 14; the tubes 120, 126 and seat 104 complete the sample loop from port 76-4 to port 76-1. The injection needle 100 has a tip that moves in and out of the injection port 134 of the seat 104 under the control of the needle drive 102. The seat 104 produces a leak-proof seal when the needle tip enters therein. In addition to controlling the movement and position of the injection needle 100 (into and out of the injection port 134), the needle drive 102 can also move the injection needle 100 in an angular direction (theta motion) between the vial 20 and the injection port 134.

The pressure source 106 produces a prescribed amount of pressure, which is measured by the transducer 108. This pressure source 106 can be a unidirectional or bidirectional peristaltic pump or a milliGAT pump, or a syringe. The wash valve 110 connects and disconnects the wash pump 112 from fluidic communication with the seat 104. When the wash valve 110 is open, the wash pump 112 can move a cleaner through the sample loop to remove any residual sample from a previous chromatography run.

Figure 4:
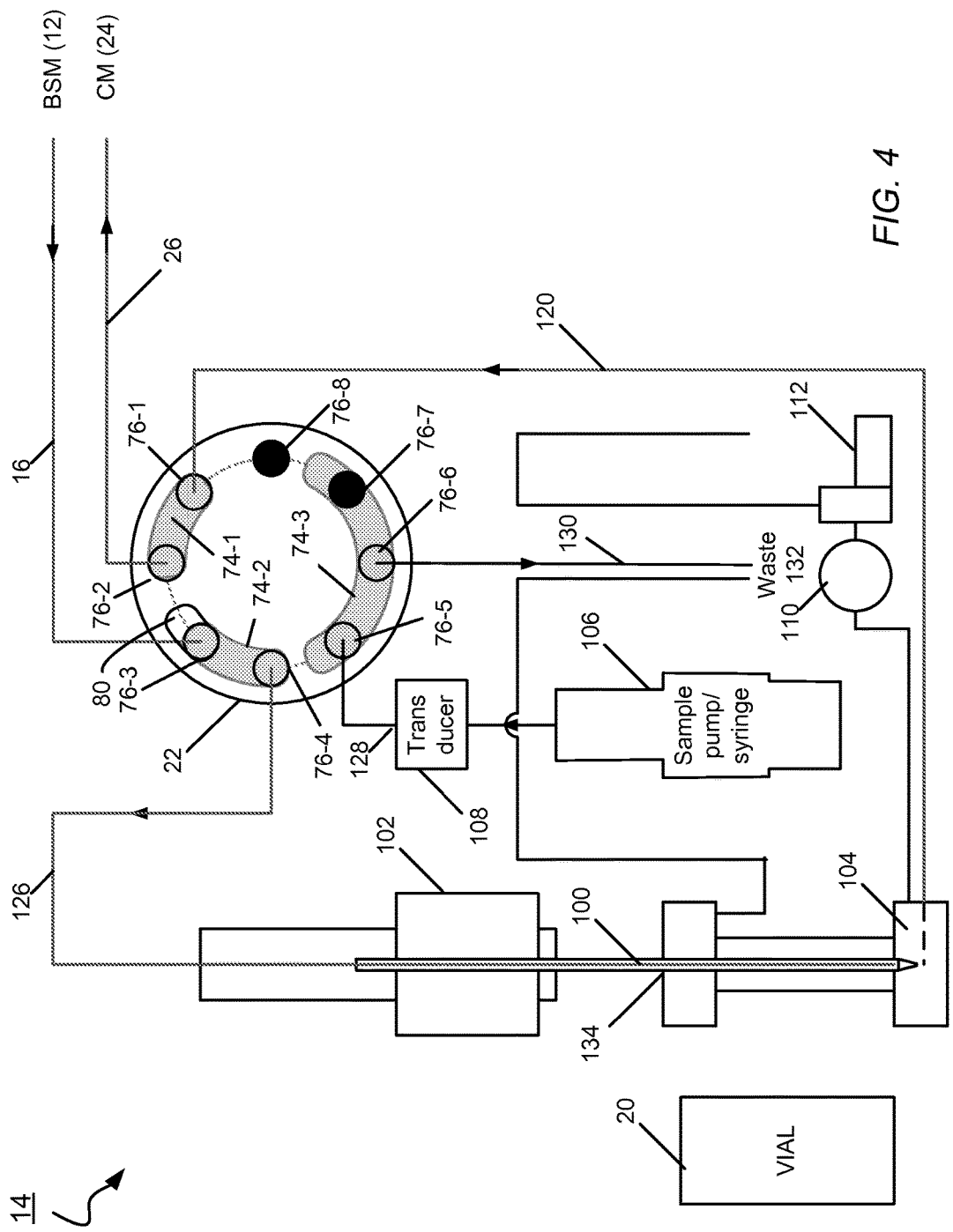
FIG. 4 is a diagram of the sample manager of FIG. 3 with the injection valve in position to direct the pressurized flow from the solvent delivery system through a sample loop.

FIG. 4 corresponds to typical operation of the sample manager 14; a continuous flow of the solvent composition stream moves from the BSM 12 to the CM 24. The orientation of the rotor 70 with respect to the stator 72 directs this solvent composition stream through the sample loop. In this orientation, the rotor groove 74-2 provides a fluidic pathway from the stator port 76-3 to the stator port 76-4, and the rotor groove 74-1 provides a fluidic pathway from the stator port 76-1 to the stator port 76-2. The solvent composition stream, arriving at the injection valve 22 from the BSM 12, enters the rotor groove 74-2 through the stator port 76-3 and exits the rotor groove 74-2 through the stator port 76-4, from which the solvent composition stream enters the sample loop. Tubing 126, the needle 100, the seat 104, and the tubing 120 comprise the sample loop (with the needle drive 102 having fully inserted the injection needle 100 into the seat 104). In FIG. 4, the sample loop does not contain any sample.

After passing through the sample loop, the solvent composition stream returns to the injection valve 22, entering the rotor groove 74-1 through the stator port 76-1. The solvent composition stream then exits the rotor groove 74-1 through the stator port 76-2, and flows through the tubing 26 towards the column manager 24.

In the orientation shown in FIG. 4, the rotor groove 74-3 provides a fluidic pathway from the stator port 76-5 to the stator port 76-6, by which the pressure source 106 (e.g., syringe) can drain or pump to waste 132.

Figure 5:
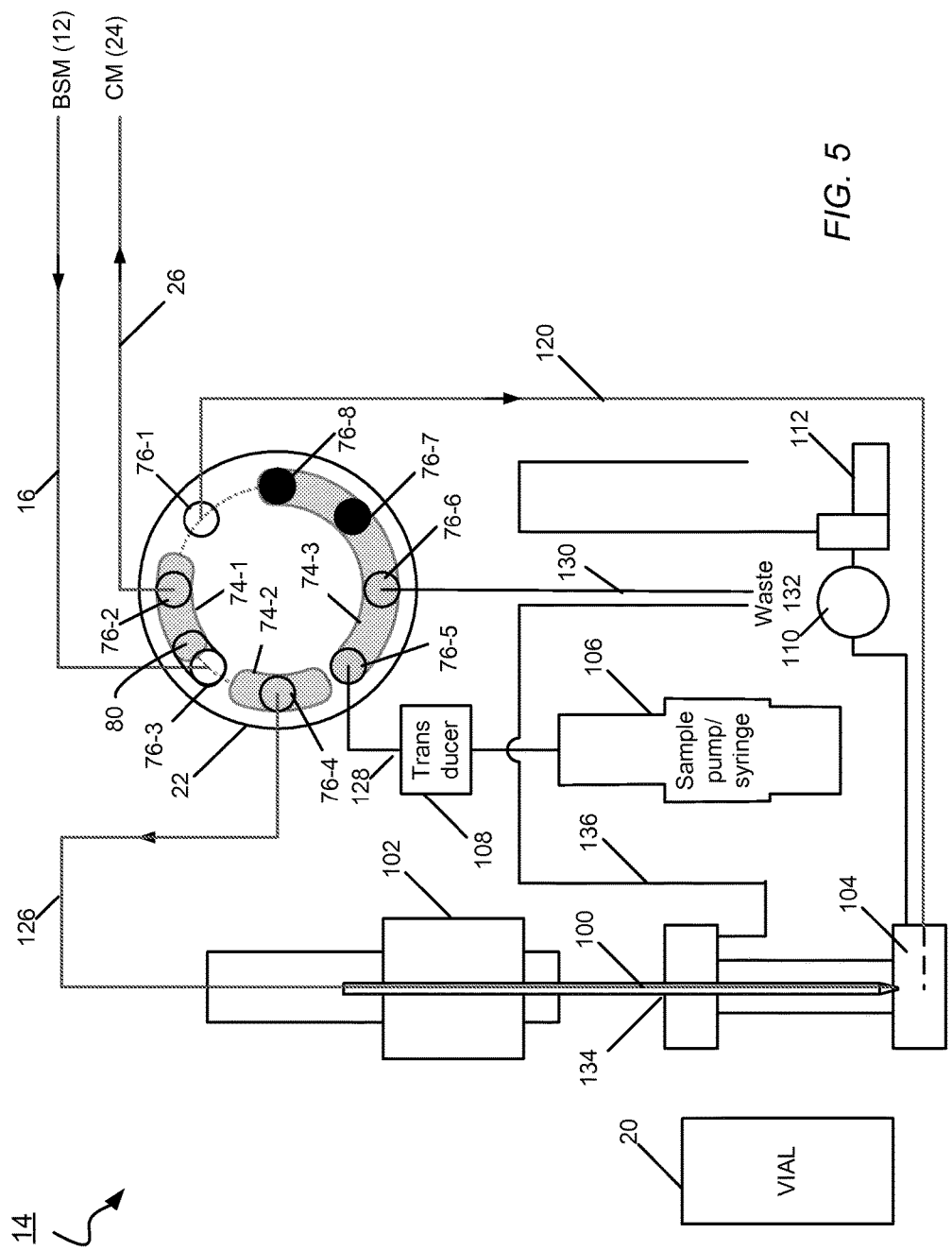
FIG. 5 is a diagram of the sample manager of FIG. 3 with the injection valve in position to direct the pressurized flow from the solvent delivery system directly to the column manager while isolating the sample loop so that the sample loop can depressurize.

FIG. 5 corresponds to the step 54 (FIG. 2) of depressurizing the sample loop prior to drawing a sample in the injection needle 100, while the pressurized solvent composition stream continues to flow from the BSM 12 to the CM 24. The orientation of the rotor 70 with respect to the stator 72 changes from the orientation in FIG. 4 counterclockwise by a half step.

In this orientation, the rotor groove 74-1 provides a fluidic pathway from the stator half-groove 80 to the stator port 76-2. Because the stator half-groove 80 connects to the stator port 76-3, the solvent composition stream, arriving through the stator port 76-3 from the BSM 12, enters the rotor groove 74-1 by way of the stator half-groove 80. The solvent composition stream then exits the rotor groove 74-1 through stator port 76-2, passing through tubing 26 towards the column manager 24. Accordingly, the flow from the BSM 12 to the CM 24 is reestablished after a momentary interruption caused by the switching of the injection valve 22 from the orientation of FIG. 4 to that of FIG. 5. This momentary interruption corresponds to the time taken to turn the rotor 70 counterclockwise by the one half-step needed for the rotor groove 74-1 to make a fluidic connection between the stator half-groove 80 and the stator port 76-2. Because the stator half-groove 80 is connected to the stator port 76-3, the fluidic connection to the stator half-groove 80 effectively establishes a fluidic connection to the stator port 76-3.

The orientation of the injection valve 22 in FIG. 5 also isolates the sample loop from the pressurized stream. The entry end of the sample loop is blocked because the rotor groove 74-2 connects to the one stator port 76-4 only; the egress end of the sample loop is blocked by having the stator port 76-1 positioned directly flush against a surface of the rotor 70. After the rotating of the rotor 70 to isolate the sample loop, the needle drive 102 partially extracts the needle 100 from the seat 104, opening a fluidic pathway to waste through tubing 136. Fluid remaining in the tubing 120, tubing 126, and injection needle 100 drains towards waste 132.

The other rotor groove 74-3 provides a fluidic pathway between stator ports 76-5 and 76-6, permitting the pressure source 106 (e.g., syringe) to continue draining or pumping into waste 132, thereby remaining primed for drawing a sample. The rotor groove 74-3 extends also to stator ports 76-7 and 76-8, but these stator ports are plugged and do not provide a flow path.

Figure 6:
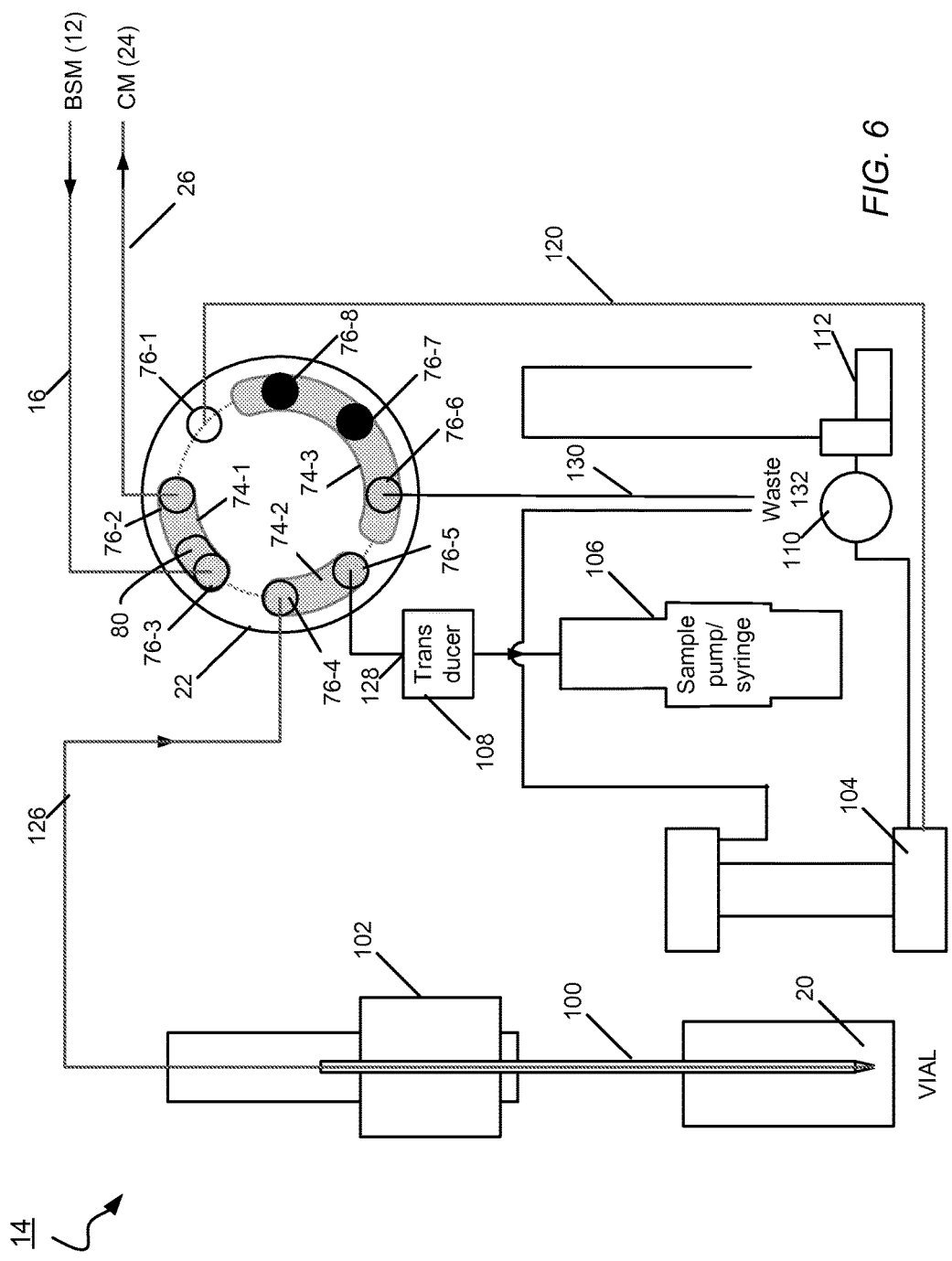
FIG. 6 is a diagram of the sample manager of FIG. 3 with the injection valve in position to draw a sample into the sample loop.

FIG. 6 corresponds to the step 56 (FIG. 2) of drawing the sample into the injection needle 100, while the pressurized solvent composition stream continues to move from the BSM 12 to the CM 24. The orientation of the rotor 70 with respect to the stator 72 changes from the orientation in FIG. 5 counterclockwise by one half step. Because of the half-step counterclockwise movement, the rotor groove 74-1 directly connects the stator port 76-3 to the stator port 76-2, providing a fluidic pathway through which the solvent composition stream continues the flow under pressure from the BSM 12 towards the column manager 24; the solvent composition stream enters the rotor groove 74-1 through stator port 76-3 and exits the rotor groove 74-1 through stator port 76-2.

This orientation of the injection valve 22 also provides a fluidic pathway from the pressure source 106 to the injection needle 100; the rotor groove 74-2 connecting stator port 76-4 to the stator port 76-5 provides this fluidic pathway. The needle drive 102 fully extracts the needle from the seat 104, and moves and lowers the needle into the vial 20 containing the sample. The operation of the pressure source 106 draws the sample up into the injection needle 100. After a prescribed amount of sample has been drawn, the pressure source 106 is turned off. The pressure source 106 may draw an amount of sample in excess of the capacity of the needle 100 and tubing 126. Such excess sample can be drawn into the rotor groove 74-2 and tubing 128.

In addition, the egress end of the sample loop remains blocked, with the stator port 76-1 still positioned directly flush against a surface of the rotor 70. Further, the other rotor groove 74-3 extends across the stator ports 76-6, 76-7, and 76-8; any fluid remaining in this groove may drain to waste 132.

Figure 7:
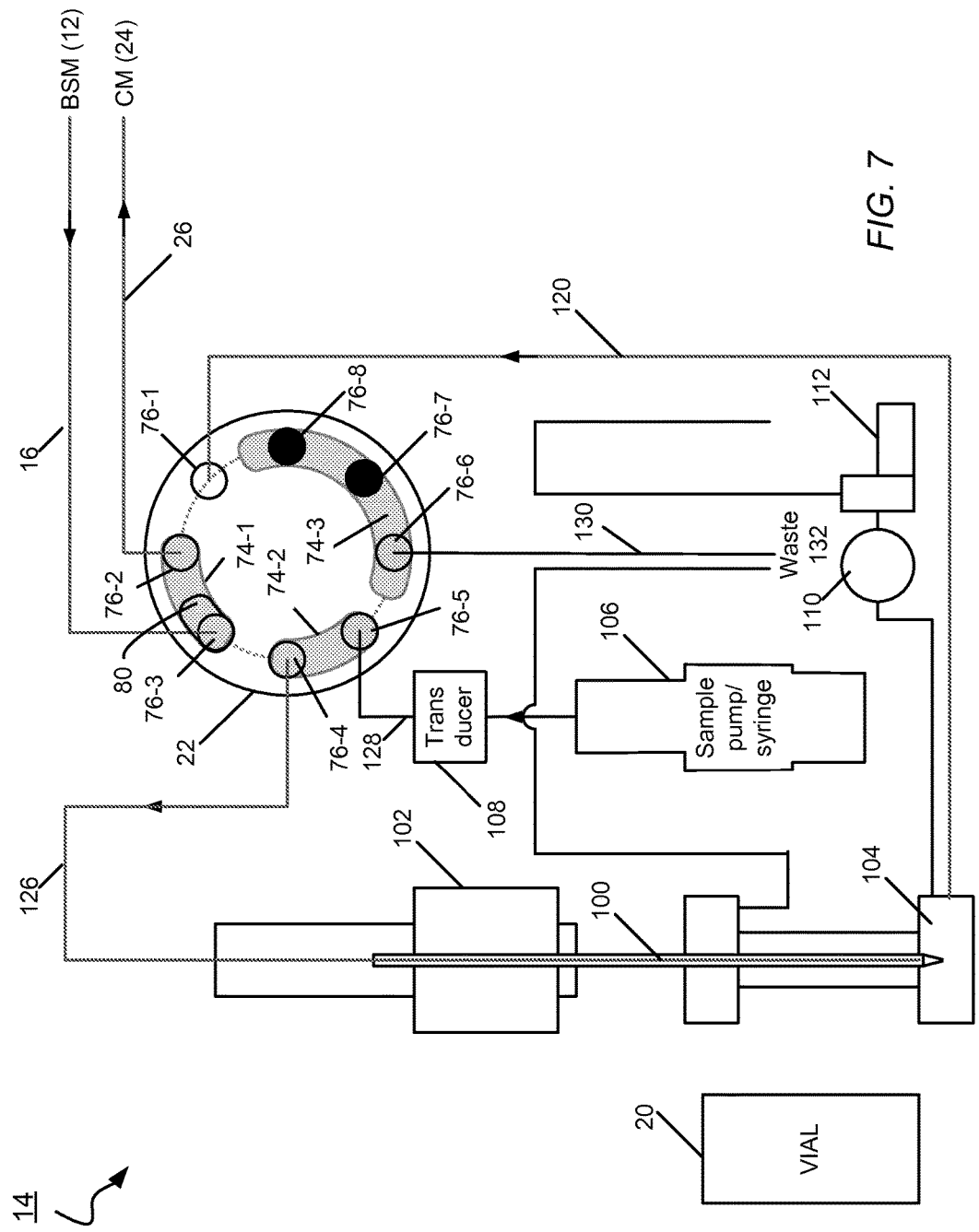
FIG. 7 is a diagram of the sample manager of FIG. 3 with the injection valve in position to pressurize the sample loop.

FIG. 7 corresponds to the optional step 58 (FIG. 2) of pressurizing the sample drawn into the injection needle 100, in order to bring the pressure of the sample nearer to the level of pressure of the solvent composition stream flowing from the BSM 12 to the CM 24. The orientation of the rotor 70 with respect to the stator 72 is unchanged from the orientation in FIG. 6.

After the pressure source 106 draws the sample into the injection needle 100, the needle drive 102 removes the injection needle 100 from the vial 20 and returns and fully inserts the needle 100 into the seat 104. The completely sealed insertion of the needle 100 restores the sample loop. The direction of operation of the pressure source 106 then reverses from that used to draw the sample, now attempting to pump the sample through the sample loop. Because the egress end of the sample loop remains blocked at the stator port 76-1, the pressure of the sample loop builds until the pressure in the sample loop reaches the capability of the pressure source 106 to further increase the pressure, or until a feedback system, based on pressure readings provided by the transducer 108, stops the pumping.

Figure 8:
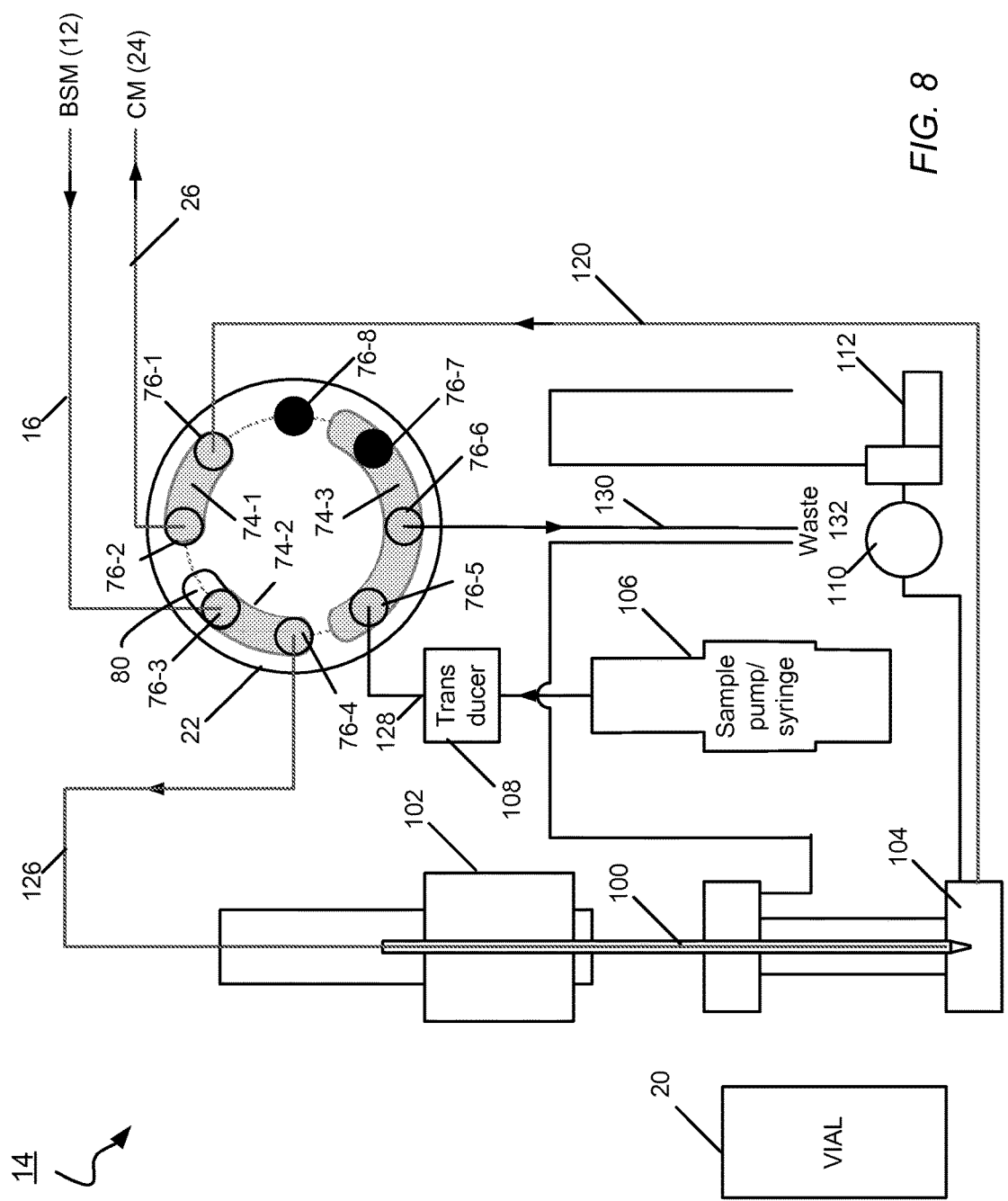
FIG. 8 is a diagram of the sample manager of FIG. 3 with the injection valve in position to direct the pressurized flow from the solvent delivery system through the sample loop containing the sample.

FIG. 8 corresponds to the step 60 (FIG. 2) of injecting the sample drawn into the sample loop into the solvent composition stream flowing from the BSM 12. The orientation of the rotor 70 with respect to the stator 72 is the same as that shown in FIG. 4. The rotor 70 turns clockwise by one full step to enter this orientation from its last position as shown in FIG. 6 (or FIG. 7).

The solvent composition stream arrives at the injection valve 22 from the BSM 12, enters the rotor groove 74-2 through the stator port 76-3, and exits the rotor groove 74-2 through stator port 76-4. The solvent composition stream then enters the sample loop now containing sample. The solvent composition stream passes into the injection needle 100, pushing the sample, and returns to the injection valve 22, entering the rotor groove 74-1 through the stator port 76-1. The solvent composition stream, pushing the sample, then exits the rotor groove 74-1 through stator port 76-2, and passes through tubing 102 towards the column manager 24. Further, any sample overfill in the tubing 128 and the pressure source 106 can drain (or be pumped) to waste 132 through the rotor groove 74-3 that provides a fluidic pathway from the stator port 76-5 to the stator port 76-6.

Although the orientation of the valve changes by one full step when introducing the sample loop into the path of the stream, the interruption of the flow from the BSM 12 to the CM 24 lasts only for the amount of time taken to turn the rotor 70 one half step clockwise. This half-step difference is because the stator half-groove 80 maintains a fluidic path between the stator port 76-3 and stator port 76-2, and, thus, the flow from the BSM 12 to the CM 24, during the first half of the clockwise turn.

Figure 9:
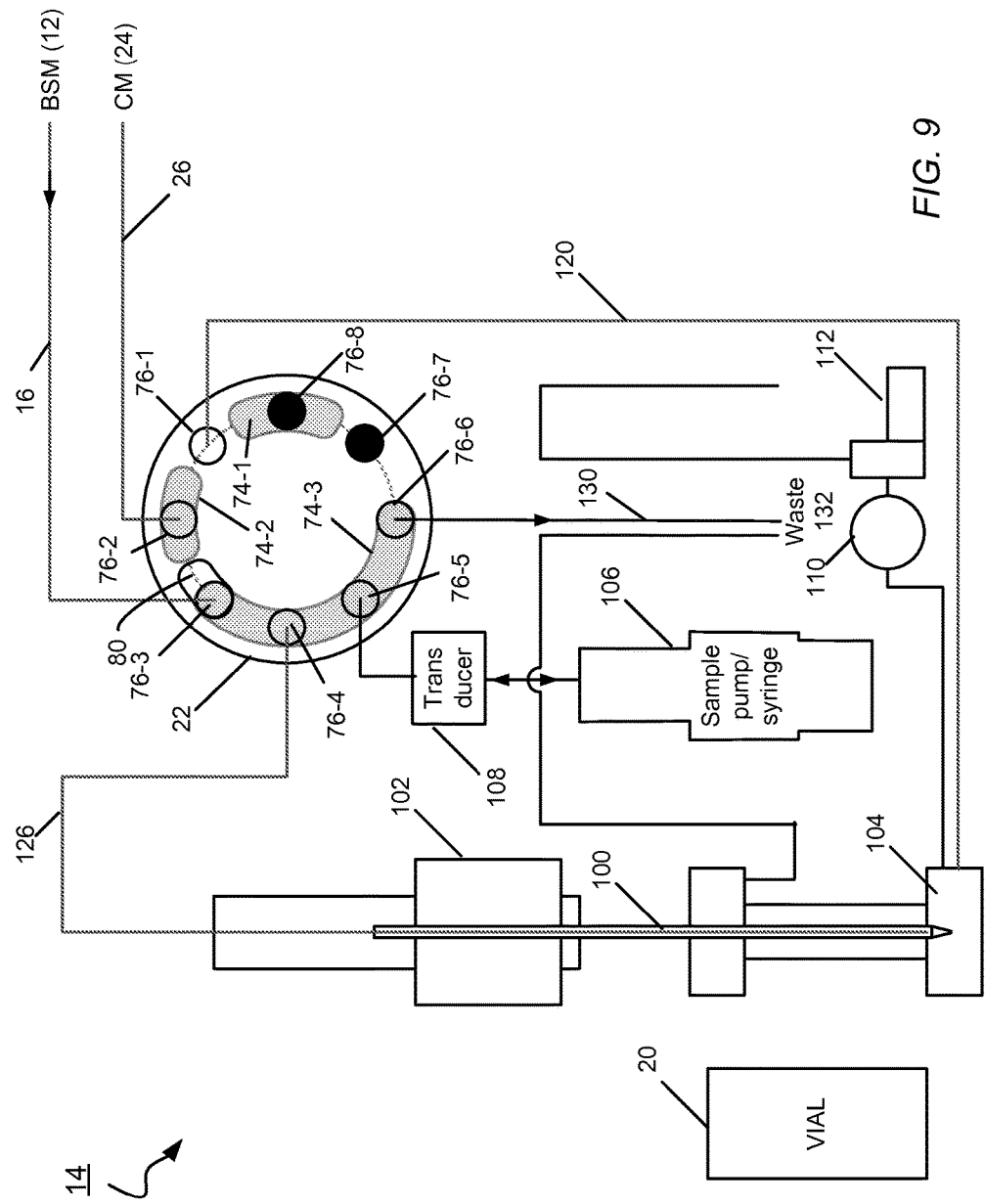
FIG. 9 is a diagram of the sample manager of FIG. 3 with the injection valve in position for priming the sample pump or syringe.
Figure 10:
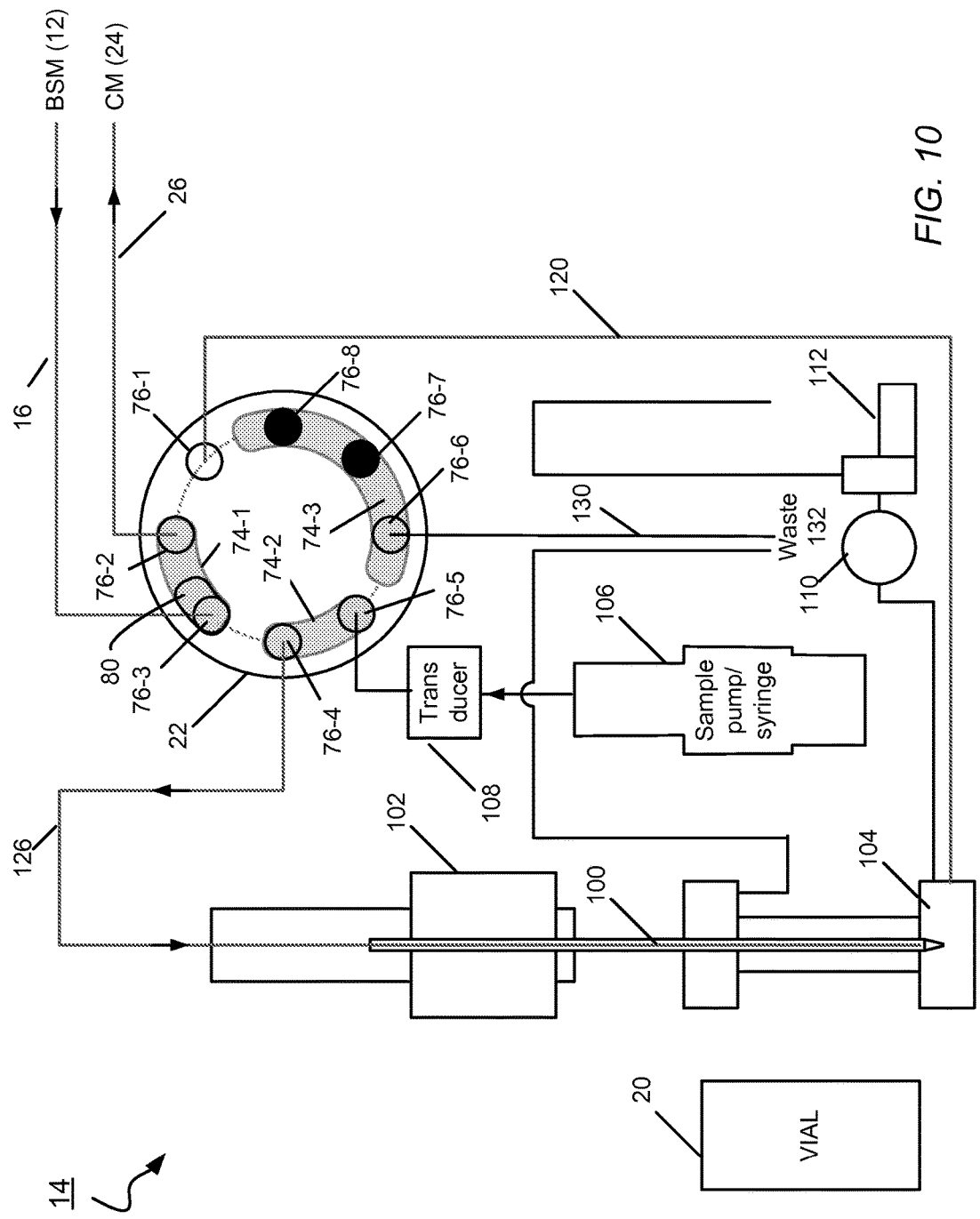
FIG. 10 is a diagram of the sample manager of FIG. 3 with the injection valve in position for performing a leak test.

FIG. 9 and FIG. 10 show configurations of the sample manager 14 for performing other functions that may affect the quality of a chromatography run. In both of these figures, the eight stator ports 76 of the injection valve 22 are connected to the various components of the SM 14 just as such stator ports 76 are connected in FIG. 4. The configuration of FIG. 9 corresponds to the purging and priming of the pressure source 16, to ensure the removal of air from the pressure source 16. The orientation of the rotor 70 with respect to the stator 72 has the rotor groove 74-3 connecting together the stator ports 76-3, 76-4, 76-5, and 76-6. The other rotor grooves 74-1, 74-2 are uninvolved in the purging and priming, with the stator port 76-2 that is coupled to the column manager 24 being isolated from the stream coming from the BSM 12. In addition, the egress end of the sample loop is blocked at the stator port 76-1.

The stream coming from the BSM 12 enters the rotor groove 74-3 through the stator port 76-3 and flows toward waste 132 through the stator port 76-6, the only open fluidic pathway permitting a flow. With the flow from the BSM 12 filling the rotor groove 74-3, a syringe (i.e., pressure source 106) can move up and down, causing any and all air bubbles in the syringe to escape into the stream flowing towards waste 132, thereby priming the syringe and readying the syringe for use.

The configuration of the sample manager 14, as shown in FIG. 10, can be used to perform a leak test. The port connections to the various SM components and the orientation of the rotor 70 with respect to the stator 72 are the same as those used to pressurize the sample loop (FIG. 7). By pressurizing the sample loop—without any sample in the loop—a technician can test the very same plumbing and SM components under the very conditions that will be used in a chromatographic run with an actual sample. This leak test can be performed between actual sample runs, to ensure a leak has not developed in the course of using the equipment.

Figure 11:
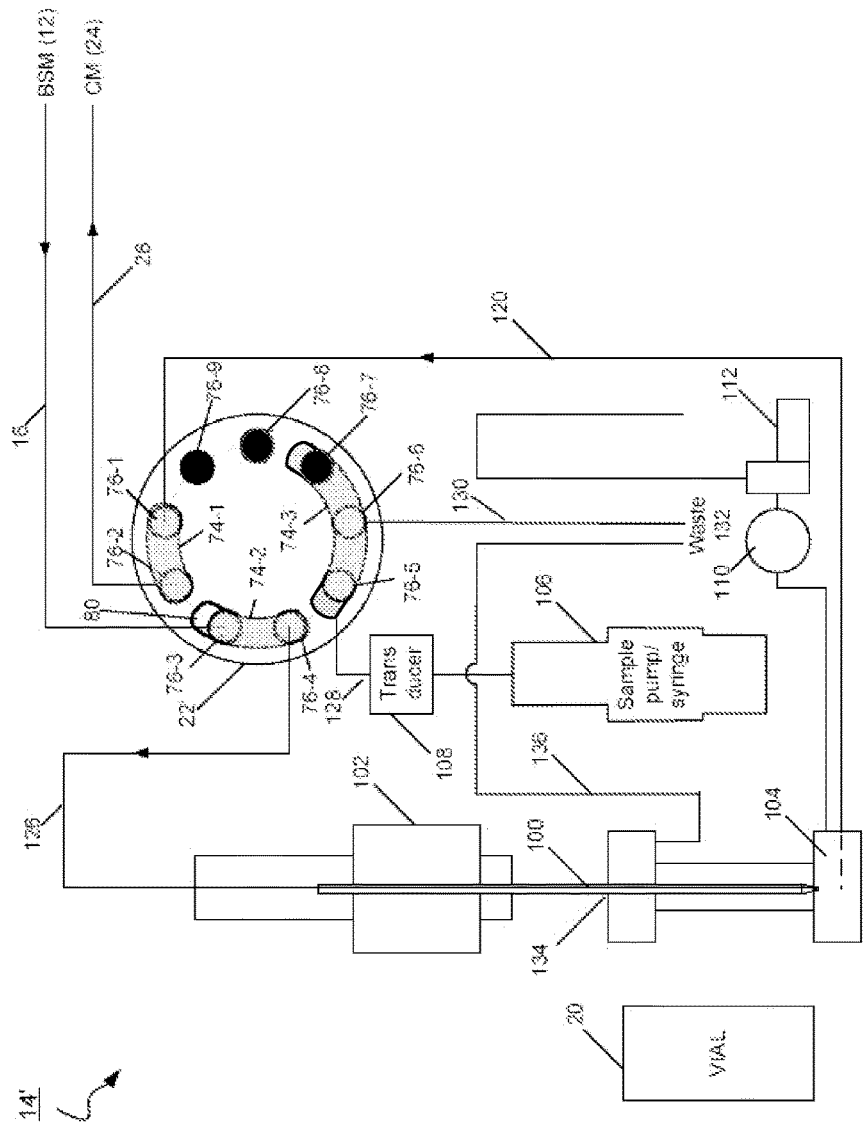
FIG. 11 is a diagram of another embodiment of a sample manager, having in this instance a nine-port injection valve configurable to serve as the sole valve needed to perform fully the sample injection sequence of FIG. 2.

FIG. 11 shows another embodiment of a SM 14' that uses a nine-port injection valve 22' to perform a full sample injection sequence. The other components of the SM 14', in particular, the flow-through needle 100, needle drive 102, seat 104, pressure source 106, transducer 108, wash valve 110 connected to a wash pump 112, and sample source 20, are the same as those components of the SM 14 described in connection with FIGS. 4-10.

In FIG. 11, the nine ports 76 of the injection valve 22' are connected to the various components of the SM 14' as follows: port 76-1 is connected by tubing 120 to an exit port of the seat 104; port 76-2 is connected by tubing 26 to the column manager 24; port 76-3 is connected by tubing 16 to the solvent delivery system 12; port 76-4 is connected by tubing 126 to the entry end of the needle 100; port 76-5 is connected by tubing 128 to the transducer 108; port 76-6 is connected by tubing 130 to waste 132; ports 76-7, 76-8, and 76-9 are unused and plugged.

Like the 8-port injection valve 22 of the sample manager 14, the injection valve 22' of the sample manager 14' has a rotor with three arcuate flow-through channels or grooves 74-1, 74-2, and 74-3 disposed in an asymmetrical pattern on a radius of the rotor. Similar to the 8-port injection valve 22, the channels can be 0.008" in width, 0.008" in depth, with a 0.004" radius at the bottom of the groove.

The stator has nine stator ports 76-1, 76-2 . . . 76-9 symmetrically disposed along a radius of the stator. The additional ninth port 76-9 (compared to the injection valve 22) is disposed between the first stator port 76-1 and the eight stator port 76-8. Because of the additional ninth port 76-9, the arc distance between two neighboring stator ports of the injection valve 22' is less than that between two neighboring stator ports of the injection valve 22 of FIGS. 4-10. Like the stator of the injection valve 22, the stator of the injection valve 22' also has the groove 80 connected to the stator port 76-3, with a length that spans half the distance between, and inclusive of, the two adjacent stator ports 76-2 and 76-3.

Like the 8-port injection valve 22 of the sample manager 14, the rotor groove 74-3 of the injection valve 22' is longer than the other two rotor grooves 74-1, 74-2, which are equal in length; the rotor grooves 74-1 and 74-2 each spans the distance between (and including) two stator ports; the rotor groove 74-3 spans four stator ports. The length of each rotor groove 74-1, 74-2 is sufficient to connect together two adjacent stator ports 76; the length of rotor groove 74-3 connects together four neighboring stator ports 76.

In FIG. 11, the nine-port injection valve 22' is positioned to direct a continuous flow of pressurized solvent composition stream moves from the BSM 12 to the CM 24 through the sample loop. The orientation of the rotor with respect to the stator can change to produce each of the operations attained by the injection valve 22 of the SM 14, namely, to direct depressurize a sample loop to load a sample therein, to pressurize the sample loop containing the sample, to inject the sample into a flowing solvent composition, to purge the sample syringe, and to perform leak tests. The nine-port injection valve 22' shows that other embodiments of injection valves can be configured to serve as the only valve used to fully perform an injection sequence in accordance with the principles described herein.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable storage medium(s) may be utilized. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code embodied on a computer readable medium may be transmitted using any appropriate medium, including but not limited to wireless, wire-line, optical fiber cable, RF, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages.

Aspects of the present invention are described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable storage medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It is to be understood that such terms like above, below, upper, lower, left, leftmost, right, rightmost, top, bottom, front, and rear are relative terms used for purposes of simplifying the description of features as shown in the figures, and are not used to impose any limitation on the structure or use of any thermal systems described herein. While the invention has been shown and described with reference to specific embodiments, it should be understood by those skilled in the art that various changes in form and detail may be made therein without departing from the spirit and scope of the invention as defined by the following claims.

What is claimed is:

1. A sample manager comprising:
   a sample loop; and
   a single injection valve configured to (i) depressurize the sample loop, (ii) draw a sample into the sample loop, and (iii) inject the sample in the sample loop into a pressurized fluidic stream, the injection valve having a stator and a rotor rotatably fitted to the stator, the stator having a plurality of stator ports arranged on the stator, the stator further including a stator groove connected at one end to a first one of the stator ports and terminating at an opposite end between the first stator port and a second one of the stator ports adjacent to the first stator port, the first stator port being fluidically coupled to a source of the pressurized fluidic stream, the second stator port being fluidically coupled to a destination of the pressurized fluidic stream, the rotor having a plurality of rotor grooves arranged in an asymmetrical pattern on the rotor, each of the rotor grooves connecting to one or more of the stator ports,
   wherein one of the rotor grooves has a length sufficient to connect together four adjacent stator ports and wherein the injection valve has at least three different positions including a first position in which a first one of the rotor grooves connects the stator groove to the second stator port to enable the pressurized fluidic stream arriving at the first stator port to flow directly to the second stator port towards the destination while the sample loop depressurizes.

2. The sample manager of claim 1, further comprising:
   a flow-through needle connected to a third one of the stator ports;
   a pressure source connected to a fourth one of the stator ports, and
   wherein the at least three different positions of the injection valve includes a second position in which the first rotor groove connects the first stator port to the second stator port to enable the pressurized fluidic stream arriving at the first stator port to flow directly to the second stator port and a second one of the rotor grooves connects the third stator port to the fourth stator port to enable the pressure source to draw the sample from a sample source into the flow-through needle.

3. The sample manager of claim 2, further comprising:
   a seat into which the flow-through needle is driven and sealed, an outlet of the seat being connected to a fifth one of the stator ports, and
   wherein the at least three different positions of the injection valve includes a third position in which the second rotor groove connects the first stator port to the third stator port to enable the pressurized fluidic stream arriving at the first stator port to flow into the flow-through needle containing the sample and the first rotor groove connects the fifth stator port to the second stator port to enable the pressurized fluidic stream containing the sample to exit the sample loop and flow towards the destination.

4. The sample manager of claim 3, wherein, while the injection valve is in the second position and the flow-through needle is driven into and sealed by the seat, the pressure source pressurizes the sample loop containing the sample before the injection valve moves to the third position to inject the sample to the pressurized fluidic stream.

5. The sample manager of claim 1, further comprising:
a flow-through needle connected to a third one of the stator ports adjacent the first stator port;
a waste receptacle connected to a fourth one of the stator ports;
a pressure source connected to a fifth one of the stator ports disposed between the third and fourth stator ports;
a seat into which the flow-through needle is driven and sealed, an outlet of the seat being connected to a sixth one of the stator ports; and
wherein the at least three different positions of the injection valve includes a second position in which the sixth stator port is blocked, thereby blocking a flow through the sample loop, and wherein a second one of the rotor grooves connects the first, third, fourth, and fifth stator ports to enable the pressurized fluidic stream arriving at the first stator port to flow towards the waste receptacle through the fourth stator port so the pressure source can be primed.

6. The sample manager of claim 1, wherein the asymmetrical pattern of the rotor grooves on the rotor is produced by at least one of the rotor grooves having a different length than at least one of the other rotor grooves.

7. The sample manager of claim 1, wherein the asymmetrical pattern of the rotor grooves on the rotor is produced by at least one gap between neighboring rotor grooves being greater than at least one other gap between neighboring rotor grooves.

8. The sample manager of claim 1, wherein the stator has eight stator ports.

9. A method of completely performing a chromatography injection sequence using only a single rotary valve having a stator and a rotor rotatably fitted to the stator, the stator having a plurality of stator ports arranged on the stator, the stator further including a stator groove connected at one end to a first one of the stator ports, an opposite end of the stator groove terminating between the first stator port and a second one of the stator ports that is adjacent to the first stator port, a third one of the stator ports being connected to an inlet of a sample loop, a fourth one of the stator ports being connected to an outlet of the sample loop, the rotor having a plurality of rotor grooves arranged in an asymmetrical pattern on the rotor, each of the rotor grooves connecting to one or more of the stator ports, the method comprising:
delivering a pressurized fluidic stream to the first stator port;
fluidically coupling the second stator port to a destination of the pressurized fluidic stream;
placing the rotary valve into a first position in which a first one of the rotor grooves connects the stator groove to the second stator port to cause the pressurized fluidic stream arriving at the first stator port to flow through the stator groove directly to the second stator port and towards the destination, while the first position of the rotary valve blocks the inlet and outlet of the sample loop, enabling the sample loop to depressurize;
changing the rotary valve from the first position to a second position in which the first rotor groove connects the first stator port to the second stator port to cause the pressurized fluidic stream arriving at the first stator port to flow directly to the second stator port, while enabling a sample to be drawn into the sample loop; and
changing the rotary valve, by turning the rotary valve one-half step, from the second position to a third position to redirect the pressurized fluidic stream arriving at the first stator port through the sample loop containing the sample before the pressurized fluidic stream flows to the second stator port towards the destination.

10. The method of claim 9, wherein changing the rotary valve from the second position to the third position includes turning the rotary valve one full step in a direction opposite a direction used to change the rotary valve from the first position to the second position.

11. The method of claim 9, further comprising pressurizing the sample loop containing the sample while the rotary valve is in the second position before changing the rotary valve to the third position to inject the sample into the pressurized fluidic stream.

12. The method of claim 9, further comprising:
connecting a flow-through needle to a third one of the stator ports;
connecting a pressure source to a fourth one of the stator ports; and
wherein, while the rotary valve is in the second position, a second one of the rotor grooves connects the third stator port to the fourth stator port, a tip of the flow-through needle is inserted into a source of sample, and the pressure source draws the sample from the source through the tip into the flow-through needle.

13. The method of claim 12, further comprising:
driving the flow-through needle into a seat to produce a seal, the seat having an outlet connected to a fifth one of the stator ports; and
wherein, while the rotary valve is in the third position, the second rotor groove connects the first stator port to the third stator port to enable the pressurized fluidic stream arriving at the first stator port to flow into the flow-through needle containing the sample, and first rotor groove connects the fifth stator port to the second stator port to enable the pressurized fluidic stream containing the sample to exit the sample loop and flow towards the destination.

14. The method of claim 9, further comprising:
connecting a third one of the stator ports, adjacent the first stator port, to a flow-through needle;
connecting a fourth one of the stator ports to a waste receptacle;
connecting a fifth one of the stator ports, disposed between the third and fourth stator ports, to a pressure source;
connecting a sixth one of the stator ports to an outlet of a seat;
driving the flow-through needle into the seat to produce a seal;
turning the rotary valve to the second position in which a sixth stator port is blocked, thereby blocking a flow through the sample loop, and wherein a second one of the rotor grooves connects the first, third, fourth, and fifth stator ports to enable the pressurized fluidic stream arriving at the first stator port to flow towards the waste receptacle through the fourth stator port; and priming the pressure source while the injection valve is in the second position.

15. The method of claim 9, further comprising:
connecting a third one of the stator ports, adjacent the first stator port, to a flow-through needle;
connecting a fourth one of the stator ports to a pressure source;
connecting a fifth one of the stator ports to an outlet of a seat;
driving the flow-through needle into an inlet of the seat to produce a seal; and
turning the injection valve from the first position into a second position in which the first rotor groove connects the first stator port to the second stator port to enable the pressurized fluidic stream arriving at the first stator port to flow directly to the second stator port, in which a second one of the rotor grooves connects the third stator port to the fourth stator port connected to the pressure source, and in which the fifth stator port connected to the outlet of the seat is blocked; and
performing a leak test by pressurizing the sample loop using the pressure source.

16. A rotary valve used in chromatography, comprising:
a stator having a plurality of stator ports arranged on the stator, the stator further including a stator groove, one end of the stator groove connecting to a first one of the stator ports and an opposite end of the stator groove terminating between the first stator port and a second one of the stator ports adjacent to the first stator port; and
a rotor rotatably fitted to the stator, the rotor having a plurality of rotor grooves arranged in an asymmetrical pattern on the rotor, each of the rotor grooves connecting to one or more of the stator ports, wherein one of the rotor grooves has a length sufficient to connect together four adjacent stator ports and wherein different connections of the rotor grooves to the stator ports produce at least three different positions for the rotary valve, the three different positions of the rotary valve providing a complete chromatography sample injection sequence using only a single valve.

17. The rotary valve of claim 16, wherein the asymmetrical pattern of the rotor grooves on the rotor is produced by at least one of the rotor grooves having a different length than at least one of the other rotor grooves.

18. The rotary valve of claim 16, wherein the asymmetrical pattern of the rotor grooves on the rotor is produced by at least one gap between neighboring rotor grooves being greater than at least one other gap between neighboring rotor grooves.

19. The rotary valve of claim 16, wherein the stator has eight stator ports.

* * * * *